United States Patent [19]
Matson

[11] Patent Number: 6,090,553
[45] Date of Patent: Jul. 18, 2000

[54] USE OF URACIL-DNA GLYCOSYLASE IN GENETIC ANALYSIS

[75] Inventor: Robert S. Matson, Orange, Calif.

[73] Assignee: Beckman Coulter, Inc., Fullerton, Calif.

[21] Appl. No.: 08/959,853

[22] Filed: Oct. 29, 1997

[51] Int. Cl.[7] .............................. C12Q 1/68; C12P 19/34; C12N 9/16; G01N 27/26
[52] U.S. Cl. ............................ 435/6; 435/91.1; 435/91.2; 435/183; 435/196; 204/182.8
[58] Field of Search .................................. 435/6, 5, 91.2, 435/91.1, 4, 183, 196; 204/182.8; 935/77.78

[56] References Cited

U.S. PATENT DOCUMENTS

| | | | |
|---|---|---|---|
| 4,683,195 | 7/1987 | Mullis et al. | 435/6 |
| 4,800,159 | 1/1989 | Mullis et al. | 435/6 |
| 4,965,188 | 10/1990 | Mullis et al. | 435/6 |
| 5,035,996 | 7/1991 | Hartley | 435/6 |
| 5,104,792 | 4/1992 | Silver et al. | 435/6 |
| 5,599,672 | 2/1997 | Liang et al. | 435/6 |

FOREIGN PATENT DOCUMENTS

97/03210  1/1997  WIPO ........................................ 435/6

OTHER PUBLICATIONS

Promotional Materials, BESS T–Scan™ Mutation Detection & Localization Kit Flyer, Epicentre Technologies, received Sep. 29, 1997.

Kinard et al. Abstr Gen Meet. Am Soc Microbiol 92: 116 (abstract provided), 1992.

Hawkins et al., Nature Biotechnol. 15:803–804, Aug. 1997.

*Primary Examiner*—Stephanie Zitomer
*Attorney, Agent, or Firm*—William H. May; Margaret A. Kivinski

[57] ABSTRACT

The present invention relates to a process for detecting the presence of at least one specific nucleic acid sequence in a sample containing a nucleic acid or a mixture of nucleic acids by amplifying the nucleic acid using polymerase chain reaction, cleaving the amplified products with uracil DNA glycosylase to obtain short DNA segments and detecting the DNA fragments by using reverse blot hybridization.

27 Claims, 7 Drawing Sheets

Figure 1

UDG Hydrolysis Fragment Hybridization

GACGGAATATAAGCTGGTGGTGGTGGGCGCCG (G->T) C codon 12

GTGTGGGCAAGAGTGCGCTGACCATCCAGCTGAT

CCAGAACCATTTTGTGGACGAATACGACCCCAC

TATAGAG

H-ras 109 bp amplicon (sense strand)

GACGGAA|A|AAGC|GG|GG|GG|GGGCGCCGGCG 12 mer

G|G|GGGCAAGAG|GCGC|GACCA|CCAGC|GA|

CCAGAACCA|||G|GGACGAA|ACGACCCCAC

|A|AGAG wild type fragment pattern

GACGGAA|A|AAGC|GG|GG|GG|GGGCGCCG|CG 8 mer

G|G|GGGCAAGAG|GCGC|GACCA|CCAGC|GA|

CCAGAACCA|||G|GGACGAA|ACGACCCCAC

|A|AGAG mutant fragment pattern

|= site of UDG hydrolysis of uracil

Figure 2

UDG Hydrolysis Fragment Hybridization

CTCTATAGTGGGGTCGTATTCGTCCACAAAATGGTTCTGGATCA

GCTGGATGGTCAGCGCACTCTTGCCCACA<u>C</u>CGCCGGCGCCCACCA codon 12

H-ras 109bp amplicon (antisense)

C|C|A|AG|GGGG|CG|A||CG|CCACAAAA|GG||C|GGA|CA

GC|GGA|GG|CAGCGCAC|C||<u>GCCCACACCGCCGGCGCCCACCA</u>

31 mer

<u>CCACCAGC</u>||A|A||CCG|C wild type fragment pattern

C|C|A|AG|GGGG|CG|A||CG|CCACAAAA|GG||C|GGA|CA

GC|GGA|GG|CAGCGCAC|C||<u>GCCCACAACGCCGGCGCCCACC</u>

31 mer

<u>ACCACCAGC</u>||A|A||CCG|C mutant fragment pattern

| = site of UDG hydrolysis of uracil

AGAROSE GEL ELECTROPHORESIS

UDG FRAGMENT HYBRIDIZATION

Figure 5

SEQUENCE LISTING (1) GENERAL INFORMATION:
    (I) APPLICANT: Robert S. Matson
    (ii) TITLE OF INVENTION: USE OF URACIL-DNA GLYCOSYLASE IN GENETIC ANALYSIS
    (iii) NUMBER OF SEQUENCES: 10
    (iv) CORRESPONDENCE ADDRESS:
        (A) ADDRESSEE: Beckman Instruments, Inc.
        (B) STREET: 2500 Harbor Boulevard
        (C) CITY: Fullerton
        (D) STATE: California
        (E) ZIP: 92834-3100
    (v) COMPUTER READABLE FORM:
        (A) MEDIUM TYPE: Diskette, 3.50 inch, 1.44 Mb storage
        (B) COMPUTER: IBM compatible
        (C) OPERATING SYSTEM: WINDOWS 95 - WORDPERFECT 7.0
        (D) SOFTWARE: ASCII (DOS) TEXT
    (vi) CURRENT APPLICATION DATA:
        (A) APPLICATION NUMBER: not assigned
        (B) FILING DATE: herewith
        (C) CLASSIFICATION: not assigned
    (viii) ATTORNEY/AGENT INFORMATION:
        (A) NAME: P.R. Harder
        (B) REGISTRATION NUMBER: 20,022
        (C) REFERENCE/DOCKET NUMBER: 45D-1566
    (ix) TELECOMMUNICATION INFORMATION:
        (A) TELEPHONE: (714) 773-6929
        (B) TELEFAX: (714) 773-7936

(2) INFORMATION FOR SEQ ID NO. 1:
    (I) SEQUENCE CHARACTERISTICS:
        (A) LENGTH: 11 base pairs
        (B) TYPE: nucleic acid
        (C) STRANDEDNESS: single
        (D) TOPOLOGY: linear
    (ii) MOLECULE TYPE: DNA (genomic)
    (ix) SEQUENCE DESCRIPTION: SEQ ID NO. 1:
GGGCGCCGGC G          11

(3) INFORMATION FOR SEQ ID NO. 2:
    (I) SEQUENCE CHARACTERISTICS:
        (A) LENGTH: 8 base pairs
        (B) TYPE: nucleic acid
        (C) STRANDEDNESS: single
        (D) TOPOLOGY: linear
    (ii) MOLECULE TYPE: DNA (genomic)
    (ix) SEQUENCE DESCRIPTION: SEQ ID NO. 2:
GGGCGCCG          8

(4) INFORMATION FOR SEQ ID NO. 3:
  (I) SEQUENCE CHARACTERISTICS:
    (A) LENGTH: 31 base pairs
    (B) TYPE: nucleic acid
    (C) STRANDEDNESS: single
    (D) TOPOLOGY: linear
  (ii) MOLECULE TYPE: DNA (genomic)
  (ix) SEQUENCE DESCRIPTION: SEQ ID NO. 3:
GCCCACACCG CCGGCGCCCA CCACCACCAG C                             31

(5) INFORMATION FOR SEQ ID NO. 4:
  (I) SEQUENCE CHARACTERISTICS:
    (A) LENGTH: 31 base pairs
    (B) TYPE: nucleic acid
    (C) STRANDEDNESS: single
    (D) TOPOLOGY: linear
  (ii) MOLECULE TYPE: DNA (genomic)
  (ix) SEQUENCE DESCRIPTION: SEQ ID NO. 4:
GCCCACAACG CCGGCGCCCA CCACCACCAG C                             31

(6) INFORMATION FOR SEQ ID NO. 5:
  (I) SEQUENCE CHARACTERISTICS:
    (A) LENGTH: 11 base pairs
    (B) TYPE: nucleic acid
    (C) STRANDEDNESS: single
    (D) TOPOLOGY: linear
  (ii) MOLECULE TYPE: DNA (genomic)
  (ix) SEQUENCE DESCRIPTION: SEQ ID NO. 5:
ACGCCACCAG C                                                    11

(7) INFORMATION FOR SEQ ID NO. 6:
  (I) SEQUENCE CHARACTERISTICS:
    (A) LENGTH: 11 base pairs
    (B) TYPE: nucleic acid
    (C) STRANDEDNESS: single
    (D) TOPOLOGY: linear
  (ii) MOLECULE TYPE: DNA (genomic)
  (ix) SEQUENCE DESCRIPTION: SEQ ID NO. 6:
ACGCCAACAG C                                                    11

(8) INFORMATION FOR SEQ ID NO. 7:
  (I) SEQUENCE CHARACTERISTICS:
    (A) LENGTH: 15 base pairs
    (B) TYPE: nucleic acid
    (C) STRANDEDNESS: single
    (D) TOPOLOGY: linear
  (ii) MOLECULE TYPE: DNA (genomic)
  (ix) SEQUENCE DESCRIPTION: SEQ ID NO. 7:
AGGAAACACC AAAGA                                                15

(9)   INFORMATION FOR SEQ ID NO. 8:

(I) SEQUENCE CHARACTERISTICS:

(A) LENGTH: 12 base pairs (B) TYPE: nucleic acid (C) STRANDEDNESS: single (D) TOPOLOGY: linear (ii) MOLECULE TYPE: DNA (genomic)

(ix) SEQUENCE DESCRIPTION: SEQ ID NO. 8:

| | |
|---|---:|
| AGGAAACACC AA | 12 |

(10)   INFORMATION FOR SEQ ID NO. 9:

(I) SEQUENCE CHARACTERISTICS:

(A) LENGTH: 108 base pairs (B) TYPE: nucleic acid (C) STRANDEDNESS: single (D) TOPOLOGY: linear (ii) MOLECULE TYPE: DNA (genomic)

(ix) SEQUENCE DESCRIPTION: SEQ ID NO. 9:

| | |
|---|---:|
| GACGGAATAT AAGCTGGTGG TGGTGGGCGC CGGCGTGTGG GCAAGAGTGC | 50 |
| GCTGACCATC CAGCTGATCC AGAACCATTT TGTGGACGAA TACGACCCCA | 50 |
| CTATAGAG | 8 |

(11)   INFORMATION FOR SEQ ID NO. 10:

(I) SEQUENCE CHARACTERISTICS:

(A) LENGTH: 89 base pairs (B) TYPE: nucleic acid (C) STRANDEDNESS: single (D) TOPOLOGY: linear (ii) MOLECULE TYPE: DNA (genomic)

(ix) SEQUENCE DESCRIPTION: SEQ ID NO. 10:

| | |
|---|---:|
| CTCTATAGTG GGGTCGTATT CGTCCACAAA ATGGTTCTGG ATCAGCTGGA | 50 |
| TGGTCAGCGC ACTCTTGCCC ACACCGCCGG CGCCCACCA | 39 |

USE OF URACIL-DNA GLYCOSYLASE IN GENETIC ANALYSIS

FIELD OF THE INVENTION

The present invention relates to a process for detecting the presence of at least one specific nucleic acid sequence in a sample containing a nucleic acid or a mixture of nucleic acids by amplifying the nucleic acid using polymerase chain reaction, cleaving the amplified products with uracil-DNA glycosylase (UDG) to obtain DNA segments and detecting the DNA segments by reverse blot hybridization. More particularly, the invention relates to the use of UDG in nucleic acid hybridization to increase the sensitivity of detection of a desired nucleic acid sequence.

BACKGROUND OF THE INVENTION

It has been found that a number of human diseases can be traced directly from genetic mutations. Various diagnostic assays have been developed to identify, detect and analyze unique DNA or RNA sequences or specific genes within the total DNA or RNA extracted from tissue or culture samples to determine the presence of physiological or pathological conditions. More particularly, the identification, detection and analysis of the unique DNA or RNA sequences or specific genes within the total DNA or RNA may indicate the presence of genetic disorders or cancer. In addition, infectious diseases can also be determined by the detection of DNA or RNA of the infectious agent.

Nucleic acid hybridization is used in many procedures of biotechnology and genetic engineering. Nucleic acid hybridization is a process in which single stranded nucleic acid pairs up with a complementary nucleotide sequence of another nucleic acid thereby forming a stable, double stranded DNA helix. Because of the requirement that hybridized nucleic acid strands have complementary nucleotide base sequences, hybridization processes are used to locate, detect and/or isolate specific nucleotide base sequences present on target nucleic acids.

Nucleic acid hybridization techniques have been applied to many procedures including but not limited to Southern blot detection of specific nucleic acid sequences (Southern, *J. Mol. Biol.*, 98:503–17 (1975)); hybridization of polynucleotide primers in polymerase chain reaction to amplify the specific nucleic acid sequence. (U.S. Pat. Nos. 4,683,195 and 4,683,202 and 4,800,159 to Mullis et al; *PCR Technology*, Ehrlich, ed. Stockton press (1989); Faloona et al., *Methods in Enzymol.* 155:335–50 (1987): *Polymerase Chain Reaction*, Ehrlich, eds. Cold Spring Harbor Laboratories Press (1989); Saiki et al., *Science*, 239:487–491 (1988); Ehrlich et al., *Science*, 252:1643–1650 (1991)); library screening for cloning and manipulation of nucleic acid fragments into recombinant DNA cloning vectors (Maniatis et al., *Molecular Cloning: A Laboratory Manual*, Cold Spring Harbor Laboratory, (1982)); and Ausubel et al., *Current Protocols in Molecular Biology*, John Wiley & Sons (1987)); reverse blot hybridization using oligonucleotide with polythymidylate tails (Saiki et al., *PNAS*, 86:6230–6234 (1989)); reverse blot hybridization of PCR amplicons (Yong Zhang et al., *Nuc. Acid Res.*, 19 (14):3929–3933 (1991)). All of the foregoing documents are hereby incorporated by reference.

For a method in which specificity is desired, hybridization between strands of nucleic acid that do not have complementary nucleotide base sequences should be avoided. Beck et al., *Nuc. Acid Res.*, 16:9051 (1988) and Haqqi et al., *Nuc. Acid Res.*, 16:1184 (1988).

Southern blot hybridization is a commonly used technique of nucleic acid hybridization and involves immobilizing a set of unknown target DNA molecules on a membrane and then immersing the membrane in a solution containing a labeled DNA probe molecule under conditions where the complementary molecules will anneal. Reverse blot hybridization is a modification of the Southern method. Specifically, instead of immobilizing unknown DNA, a set of well defined DNA probes is immobilized on a solid surface and the "unknown" labeled DNA is present in the liquid phase.

In instances where there are multiple possibilities of nucleic acid sequences which may be present, performing multiple assays by Southern blot hybridization is cumbersome and time consuming. However, reverse blot hybridization can be advantageously used in such instances because a large number of immobilized probes can be used with a single target sample. By decoding the hybridization pattern of the unknown DNA to positions of known sequence on a solid phase array, sequence information from several positions of the unknown DNA target can be obtained. Moreover, immobilized probe formats have great potential even in situations where the number of samples and probes are approximately equal because many filters can be prepared at one time and stored until needed. With the reverse blot, analysis of all the mutations with one filter is advantageous and saves considerable time and effort.

If a desired nucleic acid sequence is present in a small amount or the background caused by similar sequences in a sample is high, it can be difficult to obtain a reliable and sensitive detection of the targeted sequence. Amplification of the target nucleic acid by a process known as polymerase chain reaction (PCR) can be advantageously used in such cases.

K. B. Mullis et al., U.S. Pat. Nos. 4,683,195 and 4,683,202 which are incorporated herein by reference, describes polymerase chain reaction as a method for increasing the concentration of a segment of a target sequence in a mixture of genomic DNA without cloning or purification. This process for amplifying the target sequence consists of introducing an excess of two oligonucleotide primers to the DNA mixture containing the desired target sequence, followed by a precise sequence of thermal cycling in the presence of a DNA polymerase. The two primers are complementary to their respective strands of double stranded target sequence. To effect amplification, the mixture is denatured and the primers are then annealed to their complementary sequences with the target molecule. Following annealing, the primers are extended with a polymerase so as to form a new pair of complementary strands. There can be numerous "cycles" (i.e., each denaturation, primer annealing, and polymerase extension constitutes a "cycle") to obtain a high concentration of an amplified segment of the desired target sequence. The length of the amplified segment of the desired target sequence is determined by the relative positions of the primers with respect to each other and, therefore, this length is a controllable parameter. By virtue of the repeating aspect of the process, the method is referred to as "polymerase chain reaction". Because the desired amplified segments of the target sequence become the predominant sequences (in terms of concentration) in the mixture, they are said to be "PCR amplified".

Uracil-DNA Glycosylase (UDG) or Uracil-N-Glycosylase (UNG) is an enzyme that catalyzes the release of free uracil from single stranded and double stranded DNA of greater than 6 base-pairs. This enzyme has found important use in the prevention of PCR template carry over contamination. PCR reactions are run in the presence of 2'-deoxyuridine 5'- triphosphate (dUTP) instead of 2'-deoxythymidine 5'- triphosphate (dTTP). The resulting dUTP-amplicon can be analyzed in a normal manner. However, to prevent the transfer of the amplicon into other PCR reactions, UDG is added to hydrolyze the amplicon into fragments. Such fragments are unable to participate in the next round of PCR, thus arresting unwanted contamination.

Longo, et al., in *Gene* (1990) 93:125–128, describe the use of uracil-DNA glycosylase to control carry-over contamination in polymerase chain reactions. The method has two steps: (I) incorporating dUTP in all PCR products (by substituting dUTP for dTTP, or by incorporating uracil during synthesis of the oligodeoxyribonucleotide primer and (ii) treating all subsequent fully preassembled starting reactions with uracil-DNA glycosylase (UDG), followed by thermal inactivation of UDG.

Fraiser et al., U.S. Pat. No. 5,536,649 describes a method of inactivating amplicons in isothermal nucleic acid amplification such as strand displacement amplification (SDA) using UDG.

Rashtchian et al., *Anal. Biochem.*, 206:91–97 (1992) describe the use of uracil-DNA glycosylase in mediating cloning of polymerase chain reaction amplified DNA.

Urdea, U.S. Pat. No. 4,775,619 describes a method for the detection of specific nucleotide sequences using hybridization. The duplex formation of the DNA and the probe affects the spatial relationship between a label and a support and the presence or absence of a particular sequence in a sample is determined by the amount of the label released into the medium. The technique provides a cleavage site between the label and the support through duplexing of the labeled probe and DNA sample. Urdea, U.S. Pat. No. 5,380,833 is a continuation-in-part of the foregoing patent, describes a solid phase hybridization assay where the sample is digested with restriction endonuclease into fragments.

Miyada et al., U.S. Pat. No. 5,525,717 is concerned with a support bound nucleotide probe specific for *N. gonorrhoeae*. The DNA sample is cleaved to obtain fragments that contain the target polynucleotide sequence.

Conventional hybridization methods of amplicons to reverse hybridization panels can be rather inefficient and require considerable time. This is apparently due to reassociation kinetics which are more favorable in the solution phase as opposed to the solid-phase. In addition, steric hindrance, secondary structure and concentration effects may also apply. Consequently, there is a need for improving the sensitivity of the detection of amplicons by reverse blot hybridization.

SUMMARY OF INVENTION

As discussed above, a key problem in the use of reverse blot hybridization is the inability to hybridize sufficient levels of target molecules within a short period of time. Since the probe-target density is reduced, the signal intensity is likewise reduced making it at times difficult to interpret the specific signal above the noise or background signal for large DNA targets such as PCR amplicons. The present inventors have discovered that by digesting PCR amplicons with UDG, unique oligonucleotide fragments are created which greatly improve the hybridization efficiency on reverse blots of PCR amplicons. These unique oligonucleotides will hybridize easily at higher density and at a shorter time.

It is known that small targets of at least about 10 to about 20 mers hybridize well within a few minutes with good signal intensity. Thus, short targets that are substantially single stranded would be optimal. For PCR amplicons of at least about 100 to about 500 bp, fragmentation would result in an abundance of short, single stranded targets. However, commonly used means to fragment amplicons are few, i.e., site specific cleavage is generally not available unless hairpins (e.g., cleavase) or restriction sites (e.g., various restriction enzymes) are present. The present inventors have discovered that uracil DNA glycosylase (UDG) can be used to produce desired oligonucleotide targets in a unique manner.

Most DNA contains a significant level of dT distributed throughout it's sequence. As a consequence of dU substitution, the potential UDG fragmentation pattern can be predicted in advance (see the reaction depicted below). Thus, probe sequences can be designed which will efficiently capture a particular complementary oligonucleotide targets are created in this method. The hybridization rate is increased over that of the full length target normally employed.

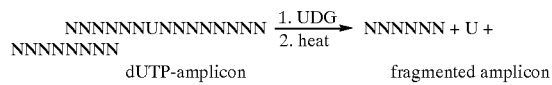

NNNNNNUNNNNNNNN $\xrightarrow[\text{2. heat}]{\text{1. UDG}}$ NNNNNN + U + NNNNNNNN dUTP-amplicon                          fragmented amplicon The present invention relates to a rapid and sensitive process for detecting the presence of at least one specific nucleic acid sequence in a sample containing a nucleic acid or a mixture of nucleic acids by amplifying the nucleic acid using polymerase chain reaction, cleaving the amplified products with uracil DNA glycosylase to obtain DNA segments and detecting the DNA segments by reverse blot hybridization.

One aspect of the invention is to provide a process for improving the hybridization efficiency on reverse blots for PCR amplicons by creating unique short oligonucleotide fragments which can more easily hybridize at higher density at a shorter time by using uracil-DNA glycosylase.

More particularly, the present invention provides a process for detecting the presence or absence of at least one specific nucleic acid sequence in a sample containing a nucleic acid or mixture of nucleic acids, or distinguishing between two different sequences in said sample, wherein the sample is suspected of containing said sequence or sequences, the process comprising the steps of:

(a) treating the sample with one oligonucleotide primer for each strand of each different specific sequence under hybridizing conditions such that, for each strand of each different sequence to which an oligonucleotide primer is hybridized, a labeled extension product of each primer is synthesized, which is complementary to each nucleic acid strand and is cleavable by a base excision repair enzyme, wherein said primer or primers are selected so as to be sufficiently complementary to each strand of each specific sequence to hybridize therewith;

(b) treating the sample under denaturing conditions to separate the labeled primer extension products from their templates forming single labeled strands;

(c) treating the sample with oligonucleotide primers such that complementary labeled primer extension products are synthesized using each of the single labeled strands produced in step (b) as a template, resulting in amplification of the specific nucleic acid sequence or sequences if present;

(d) digesting the product of step (c) with a base excision repair enzyme such that labeled oligonucleotide fragments are produced;

(e) adding the product of step (d) to at least one immobilized oligonucleotide probe for each sequence being detected capable of hybridizing to said sequence or a mutation thereof, and (f) determining whether said hybridization has occurred.

Typically, the base excision repair enzyme can be selected from the group consisting of DNA glycosylases, AP endonucleases and deoxyphosphodiesterases. Preferably, the DNA glycosylase can be selected from the group consisting of uracil-DNA glycosylase, 3-methyladenine DNA glycosylase, pyrimidine hydrate-DNA glycosylase, FaPy-DNA glycosylase and thymine mismatch-DNA glycosylase. More preferably, the DNA glycosylase is uracil-DNA glycosylase.

It is yet another object of the invention to provide simultaneous screening of multiple target sequences in a sample.

It is another object of the invention to provide a reverse blot analysis of amplified DNA fragments wherein the probes are arranged in an array.

It is another object of the invention to provide a process for detecting the presence or absence of a nucleic acid sequence containing a polymorphic restriction site specific for infectious diseases, genetic disorder or cancer which sequence is suspected of being contained in a sample.

In yet another preferred object of the invention, a process is provided for detecting the presence or absence of at least one specific nucleic acid sequence in a sample containing a nucleic acid or mixture of nucleic acids, or distinguishing between two different sequences in said sample, wherein the sample is suspected of containing said sequence or sequences, the process comprising the steps of:

(a) treating the sample with one oligonucleotide primer for each strand of each different specific sequence under hybridizing conditions such that, for each strand of each different sequence to which an oligonucleotide primer is hybridized, a labeled extension product of each primer is synthesized, which is complementary to each nucleic acid strand and is cleavable by uracil-DNA glycosylase, wherein said primer or primers are selected so as to be sufficiently complementary to each strand of each specific sequence to hybridize therewith;

(b) treating the sample under denaturing conditions to separate the labeled primer extension products from their templates forming single labeled strands;

(c) treating the sample with oligonucleotide primers such that complementary labeled primer extension products are synthesized using each of the single labeled strands produced in step (b) as a template, resulting in amplification of the specific nucleic acid sequence or sequences if present;

(d) digesting the product of step (c) with uracil-DNA glycosylase such that labeled oligonucleotide fragments are produced;

(e) adding the product of step (d) to at least one immobilized oligonucleotide probe for each sequence being detected capable of hybridizing to said sequence or a mutation thereof; and (f) determining whether said hybridization has occurred.

It is a further object of the invention to provide a diagnostic kit for the detection of at least one specific nucleic acid sequence in a sample containing one or more nucleic acids at least one of which is suspected of containing said sequence, which kit comprises in packaged form, a multi-container unit having:

a) a container for each oligonucleotide primer for each strand of each different sequence to be detected, which primer or primers are substantially complementary to each strand of each specific nucleic acid sequence such that a labeled uracil-DNA glycosylase cleavable extension product synthesized from one primer, when it is separated from its complement can serve as a template for the synthesis of the labeled extension product of the other primer;

b) a container containing an agent for polymerization;

c) a container for each of the four different nucleoside triphosphates comprising dUTP;

d) a container containing a probe capable of detecting the presence or absence of said sequence ins aid sample;

e) a container containing a means for detecting hybrids of said probe and said sequence; and f) a container of UDG.

In accordance with another aspect of the present invention, the present invention provides a process for detecting the presence or absence of at least one specific nucleic acid sequence in a sample containing a nucleic acid or mixture of nucleic acids, or distinguishing between two different sequences in said sample, wherein the sample is suspected of containing said sequence or sequences, the process comprising the steps of:

(a) treating the sample with one oligonucleotide primer for each strand of each different specific sequence under hybridizing conditions such that, for each strand of each different sequence to which an oligonucleotide primer is hybridized, a labeled extension product of each primer is synthesized, which is complementary to each nucleic acid strand and is cleavable by a base excision repair enzyme, wherein said primer or primers are selected so as to be sufficiently complementary to each strand of each specific sequence to hybridize therewith;

(b) treating the sample under denaturing conditions to separate the labeled primer extension products from their templates forming single labeled strands;

(c) treating the sample with oligonucleotide primers such that complementary labeled primer extension products are synthesized using each of the single labeled strands produced in step (b) as a template, resulting in amplification of the specific nucleic acid sequence or sequences if present;

(d) digesting the product of step (c) with a base excision repair enzyme such that labeled oligonucleotide fragments are produced;

(e) loading the product of step (d) into an electrophoresis chamber to perform electrophoretic separation of the product; and (f) determining the identity of the product by fragmentation analysis.

Typically, the electrophoretic separation can be accomplished by high resolution slab gel electrophoresis. Preferably, the electrophoretic separation is accomplished by capillary electrophoresis.

Typically, the fragmentation analysis would employ differential display pattern recognition.

These, as well as other objects and advantages are accomplished by the present invention which provides a process for detecting the presence of at least one specific nucleic acid sequence in a sample containing a nucleic acid or a mixture of nucleic acids by amplifying the nucleic acid using polymerase chain reaction, cleaving the amplified products with a base excision repair enzyme to obtain DNA segments and detecting the DNA segments by reverse blot hybridization.

BRIEF DESCRIPTION OF THE DRAWINGS

The present invention may be more fully and easily understood when taken in conjunction with the accompanying figures.

FIG. 1 illustrates UDG fragment digest pattern of H-ras sense strand in which the first listing of nucleotides is SEQ ID NO: 9, The 12 mer segment of the second nucleotides sequence is SEQ ID NO: 1, and the 8 mer segment of the third sequence listing is SEQ ID NO: 2.

FIG. 2 illustrates UDG fragment digest pattern for the H-ras antisense strand wherein the first nucleotide sequence is SEQ ID NO: 10, The 31 mer segment of the second nucleotide sequence is SEQ ID NO: 3, and the 31 mer segment of the third nucleotide sequence is SEQ ID NO: 4.

Figure 3:
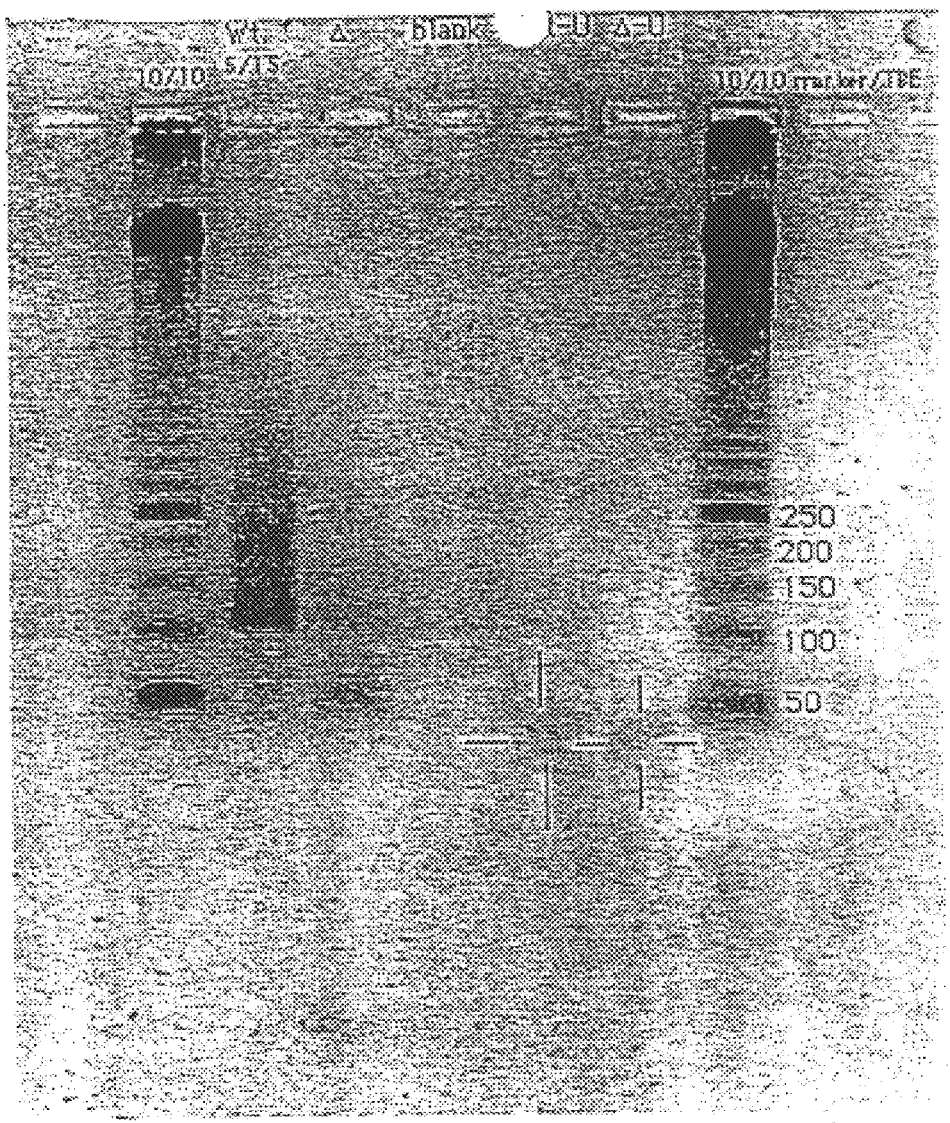
FIG. 3 illustrates a photograph of the electrophoretic pattern digests of Wt (Lane 3), Δ (Lane 4), Wt-U (Lane 6) and Δ-U (Lane 7). Lanes 2 and 8 are the standard.

The Sequence Listing contains the following:

SEQ ID No. 1: An 11 mer fragment of a 109 bp H-ras dUTP-amplicon wild type;

SEQ ID No. 2: An 8mer fragment of a 109 bp H-ras dUTP-amplicon mutant;

SEQ ID No. 3: A 31 mer fragment of a 109 bp H-ras dUTP-amplicon wild type (antisense strand);

SEQ ID No. 4: A 31 mer fragment of a 109 bp H-ras dUTP-amplicon mutant (antisense strand);

SEQ ID No. 5: An 11 mer fragment of a 157 bp K-ras dUTP-amplicon;

SEQ ID No. 6: An 11 mer fragment of a 157 bp K-ras dUTP-amplicon;

SEQ ID No. 7: A 15 mer fragment of Δ F508 dUTP-amplicon (antisense strand);

SEQ ID No. 8: A 12 mer fragment of Δ F508 dUTP-amplicon (antisense strand);

SEQ ID No. 9: A 108 mer fragment of H-ras amplicon (sense strand);

SEQ ID No. 10: A 89 mer fragment of H-ras amplicon (antisense strand).

DETAILED DESCRIPTION OF THE PREFERRED EMBODIMENTS

In the description that follows, a number of terms used in molecular biology and nucleic acid amplification technology are extensively utilized. In order to provide a clearer and consistent understanding of the specification and claims, including the scope to be given such terms, the following definitions are provided.

"Nucleotides" as used herein, is a term of art that refers to a base-sugar phosphate combination. Nucleotides are the monomeric units of nucleic acid polymers, i.e., of DNA and RNA. The term includes ribonucleoside triphosphates, such as rATP, rCTP, rGTP, or rUTP, and deoxyribonucleoside triphosphates, such as dATP, dCTP, dGTP, dUTP, or dTTP. A "nucleoside" is a base-sugar combination, i.e. a nucleotide lacking phosphate.

"Oligonucleotide" as used herein refers collectively and interchangeably to two terms of art, "oligonucleotide" and "polynucleotide". Note that although oligonucleotide and polynucleotide are distinct terms of art, there is no exact dividing line between them and they are used interchangeably herein. An oligonucleotide is said to be either an adapter, adapter/linker or installation oligonucleotide (the terms are synonymous) if it is capable of installing a desired sequence onto a predetermined oligonucleotide. An oligonucleotide may serve as a primer unless it is "blocked". An oligonucleotide is said to be "blocked," if its 3' terminus is incapable of serving as a primer.

"Oligonucleotide-dependent amplification" as used herein refers to amplification using an oligonucleotide or polynucleotide to amplify a nucleic acid sequence.

"Amplification", as used herein, refers to any in vitro process for increasing the number of copies of a nucleotide sequence or sequences, i.e., creating an amplification product which may include, by way of example additional target molecules, or target-like molecules or molecules complementary to the target molecule, which molecules are created by virtue of the presence of the target molecule in the sample. In a situation where the target is a nucleic acid, an amplification product can be made enzymatically with DNA or RNA polymerases or transcriptases. Nucleic acid amplification results in the incorporation of nucleotides into DNA or RNA. PCR is an example of a suitable method for DNA amplification. As used herein, one amplification reaction may consist of many rounds of DNA replication. For example, one PCR reaction may consist of 10–50 "cycles" of denaturation and replication.

"Amplification products", "amplified products" or "amplicons" comprise copies of the target sequence and are generated by hybridization and extension of an amplification primer. This term refers to both single stranded and double stranded amplification primer extension products which contain a copy of the original target sequence, including intermediates of the amplification reaction.

"Target" or "target sequence" refers to nucleic acid sequences to be amplified. These include the original nucleic acid sequence to be amplified, its complementary second strand and either strand of a copy of the original sequence which is produced in the amplification reaction. The target sequence may also be referred to as the template for extension of hybridized amplification primers.

"Base excision repair enzyme or (BRE)" are used herein, is a term of art that refers to enzymes which can eliminate single damaged base residues. Typically, the base excision repair enzyme can be selected from the group consisting of DNA glycosylases, AP endonucleases and deoxyphosphodiesterases. DNA glycosylases and AP endonucleases can act on spontaneous and induced DNA alterations caused by hydrolysis, oxygen free radicals and alkylating agents. Preferably, the DNA glycosylase can be selected from the group consisting of uracil-DNA glycosylase, 3-methyladenine DNA glycosylase, pyrimidine hydrate-DNA glycosylase, FaPy-DNA glycosylase and thymine mismatch-DNA glycosylase. More preferably, the DNA glycosylase is uracil-DNA glycosylase. When the enzyme is 3-methyladenine DNA glycosylase, the substrate in DNA can be 3-methylpurines, 7-methylpurines, ethylated bases, hypoxanthine or ethenoadenine. When the enzyme is pyrimidine hydrate-DNA glycosylase, the substrate in DNA can be pyrimidine residues altered by oxidative ring saturation or ting fragmentation or contraction. When the enzyme is FaPy-DNA glycosylase, the substrate in DNA can be formamidopyrimidines or 7,8 dihydro 8-oxo-guanine. When the enzyme is thymine mismatch-DNA glycosylase, the substrate in DNA can be thymine paired to guanine or uracil paired to guanine.

"AP endonuclease" as used herein, is a term of art that refers to apurinic and apyrimidinic endonucleases. When the enzyme is AP endonuclease, the substrate in DNA can be apurinic and apyrimidinic sites.

"Uracil DNA glycosylase" (UDG) or uracil-N-Glycosylase (UNG) is an enzyme that catalyzes the release of free uracil from uracil-containing DNA. It can efficiently hydrolyze uracil from single stranded, as well as double stranded DNA of greater than 6 base-pairs. E. coli UDG is preferred. Typically, uracil in DNA is recognized as a substrate whereas uracil in RNA generally is not.

"Primer" as used herein refers to an oligonucleotide or a polynucleotide that is extended by covalent addition of nucleotide monomers during amplification. The primer is preferably single-stranded. Nucleic acid amplification often is based on nucleic acid synthesis by a nucleic acid polymerase. Many such polymerases require the presence of a primer that can be extended to initiate such nucleic acid synthesis. A primer is typically 11 bases or longer; most preferably, a primer is 17 bases or longer. A minimum of 3 bases may, however, suffice.

"Primer dimer" is an extraneous DNA or an undesirable side product of PCR amplification which is thought to result from nonspecific interaction amplification primers. Primer dimers not only reduce the yield of the desired PCR product but they also compete with the genuine amplification products. Primer dimer as the name implies is a double stranded PCR product consisting of two primers and their complementary sequences. However, the designation is somewhat misleading because analysis of these products indicates that additional bases are inserted between the primers. As a result, a fraction of these artifacts may be due to spurious nonspecific amplification of similar but distinct primer binding regions that are positioned in the immediate vicinity.

"Stringency" is meant the combination of conditions to which nucleic acids are subject that cause the duplex to dissociate, such as temperature, ionic strength, and concentration of additives such as formamide. Conditions that are more likely to cause the duplex to dissociate are called "higher stringency", e.g. higher temperature, lower ionic strength and higher concentration of formamide.

The term "probe" refers to a strand of nucleic acids having a base sequence substantially complementary to a target base sequence. Typically, the probe is associated with a label to identify a target base sequence to which the probe binds, or the probe is associated with a support to bind to and capture a target base sequence. Two fundamental ways of generating oligonucleotide arrays include synthesizing the oligonucleotides on the solid phase in their respective positions; and synthesizing apart from the surface of the array matrix and attaching later are well known in the art and are incorporated herein by reference. (Southern et al., *Genomics*, 13:1008–1017(1992); Southern et al., WO89/10977). An array constructed with each of the oligonucleotides in a separate cell can be used as a multiple hybridization probe to examine the homologous sequence.

The phrase "hybridizing conditions" and its grammatical equivalents, when used with a maintenance time period, indicates subjecting the hybridization reaction admixture, in context of the concentration of the reactants and accompanying reagents in the admixture, to time, temperature, pH conditions sufficient to allow the polynucleotide probe to anneal with the target sequence, typically to form the nucleic acid duplex. Such time, temperature and pH conditions required to accomplish the hybridization depend, as is well known in the art on the length of the polynucleotide probe to be hybridized, the degree of complementarity between the polynucleotide probe and the target, the guanidine and cytosine content of the polynucleotide, the stringency of the hybridization desired, and the presence of salts or additional reagents in the hybridization reaction admixture as may affect the kinetics of hybridization. Methods for optimizing hybridization conditions for a given hybridization reaction admixture are well known in the art.

The term "label" refers to a molecular moiety capable of detection including, by way of example, without limitation, radioactive isotopes, enzymes, luminescent agents, dyes, and detectable intercalating agents. Any suitable means of detection may be employed, thus, the label maybe an enzyme label, a fluorescent label, a radioisotopic label, a chemiluminescent label, etc. Examples of suitable enzyme labels include alkaline phosphatase, acetylcholine esterase, α-glycerol phosphate dehydrogenase, alkaline phosphatase, asparaginase, β-galactosidase, catalase, δ-5-steroid isomerase, glucose oxidase, glucose-6-phosphate dehydrogenase, luciferase, malate dehydrogenase, peroxidase, ribonuclease, staphylococcal nuclease, triose phosphate isomerase, urease, and yeast alcohol dehydrogenase. Examples of suitable fluorescent labels include fluorescein label, an isothiocyanate label, a rhodamine label, a phycoerythrin label, a phycocyanin label, an allophycocyanin label, an o-phthaldehyde label, a fluorescamine label, etc. Examples of suitable chemiluminescent labels include luminal label, an aromatic acridinium ester label, an imidazole label, an acridinium salt label, an oxalate label, a luciferin label an aequorin label. Alternatively, the sample may be labeled with non-radioactive label such as biotin. The biotin labeled probe is detected via avidin or streptavidin through a variety of signal generating systems known in the art.

The term "agent" is used in a broad sense, in reference to labels, and includes any molecular moiety which participates in reactions which lead to a detectable response.

The term "support" refers to conventional supports such as beads, particles, dipsticks, fibers, filters, membranes and silane or silicate supports such as glass. In addition, support refers to porous or non-porous water insoluble material. The support can be hydrophilic or capable of being rendered hydrophilic and includes inorganic powders such as silica, magnesium sulfate and alumina; natural polymeric materials, particularly cellulosic materials and materials derived from cellulose, such as fiber containing papers, e.g., filter paper and chromatographic paper; synthetic or modified naturally occurring polymers such as nitrocellulose, cellulose acetate, poly(vinyl) chloride, polyacrylamide, crosslinked dextran, agarose, polyacrylate, polyethylene, polypropylene, poly(4-methylbutene), polystyrene, polymethacrylate, poly(ethylene terephthalate), nylon and polyvinyl butyrate. These materials can be used alone or in conjunction with other materials such as glass, ceramics, metals and the like.

The phrase "electrophoretic separation" and its grammatical equivalents, typically can be any electrophoresis method known to those skilled in the art. Preferably, the electrophoretic separation is accomplished by high resolution slab gel electrophoresis. More preferably, the electrophoretic separation is accomplished by capillary electrophoresis.

The phrase "fragmentation analysis" and its grammatical equivalents, typically can be any fragmentation analysis method known to those skilled in the art to determine the identity of a product. Preferably, the fragmentation analysis would employ differential display pattern recognition (for example, examining the difference between at least two patterns). For example, a wild type fragmentation can yield a different pattern from that of a pattern from a mutation. Thus, a mutation can be identified by comparing the wild type pattern with the mutation pattern; or by subtracting the two patterns which can yield a differential display pattern.

Polymerase Chain Reaction (PCR)

The hybridization product to be amplified functions in PCR as a primed template comprised of polynucleotide as a primer hybridized to a target nucleic acid as a template. In PCR, the primed template is extended to produce a strand of nucleic acid having a nucleotide sequence complementary to the template, i.e., template complement. Through a series of primer extension reactions, an amplified nucleic acid product is formed that contains the specific nucleic acid sequence complementary to the hybridization product.

If the template whose complement is to be produced is in the form of a double stranded nucleic acid, it is typically first denatured, usually by melting into single strands, such as single stranded DNA. The nucleic acid is then subjected to a first primer extension reaction by treating or contacting nucleic acid with a first polynucleotide synthesis primer having as a portion of its nucleotide sequence, a sequence selected to be substantially complementary to a portion of the sequence of the template. The primer is capable of initiating a primer extension reaction by hybridizing to a specific nucleotide sequence, preferably at least 8 nucleotides in length, more preferably at least 20 nucleotides in length. This is accomplished by mixing an effective amount of the primer with the template nucleic acid, and an effective amount of nucleic acid synthesis inducing agent to form the primer extension reaction admixture. The admixture is maintained under polynucleotide synthesizing conditions for a time period, which is typically predetermined, sufficient for the formation of a primer extension reaction product.

The primer extension reaction is performed using any suitable method. Generally, it occurs in a buffered aqueous solution, preferably at a pH of about 7 to 9, most preferably, about 8. Preferably, a molar excess (for genomic nucleic acid, usually $10^6:1$ primer:template) of the primer is admixed to the buffer containing the template strand. A large molar excess is preferred to improve the efficiency of the process. For polynucleotide primers of about 20 to 25 nucleotides in length, a typical ratio is in the range of about 50 ng to 1 $\mu$g., preferably about 250 ng of primer per 100 ng to about 500 ng of mammalian genomic DNA or per 10 to 50 ng of plasmid DNA.

The deoxyribonuclotide triphosphates (dNTPs), dATP, dCTP, dGTP and dUTP are also admixed to the primer extension reaction admixture to support the synthesis of primer extension products and depends on the size and number of products to be synthesized. Preferably, when uracil-DNA glycosylase enzyme is used according to the present invention, dUTP is used instead of dTTP so that subsequent treatment of the amplified product with UDG will result in the formation of oligonucleotide fragments. The invention includes the use of any analogue or derivative of dUTP which can be incorporated into the extension product and which is acted on by UDG to produce oligonucleotide fragments. The resulting solution is heated to about 90° C. to about 100° C. for about 1 to 10 minutes, preferably from 1 to 4 minutes. After heating, the solution is allowed to cool to room temperature which is preferable for primer hybridization. To the cooled mixture is added an appropriate agent for inducing or catalyzing the primer extension reaction and the reaction is allowed to occur under conditions known in the art. The synthesis reaction may occur at from room temperature up to a temperature above which the inducing agent no longer functions efficiently. Thus, for example, if DNA polymerase is used as the inducing agent, the temperature is generally no greater than about 40° C. unless the polymerase is heat stable.

The inducing agent may be any compound or system which will function to accomplish the synthesis of the primer extension products, including enzymes. Suitable enzymes for this purpose include for example *E. coli* DNA polymerase I, Klenow fragment of *E. coli* DNA polymerase I, T4 DNA polymerase, T7 DNA polymerase, recombinant modified T7 DNA polymerase, other available DNA polymerase, reverse transcriptase and other enzymes including heat stable enzymes which will facilitate the combination of nucleotides in the proper manner to form the primer extension products which are complementary to each nucleic acid strand. Heat stable DNA polymerase is used in the most preferred embodiment by which PCR is conducted in a single solution in which the temperature is cycled. Representative heat stable polymerases are DNA polymerases isolated from *Bacillus stearothermophilus* (BioRad), *Thermus Thermophilus* (FINZYME, ATCC#27634), Thermus species (ATCC #31674), *Thermus aquaticus* strain TV1151B (ATCC 25105), *Sulfolobus acidocaldarius* described by Bukrashuili et al. *Biochem. Biophys. Acta* 1008:102–7 (1989) and Elie et al. *Biochem. Biophys. Acta* 951:261–7 (1988) and *Thermus filiformis* (ATCC #43280). Particularly, the preferred polymerase is Taq DNA polymerase available from a variety of sources including Perkin Elmer Cetus (Norwak, Conn.), Promega (Madison, Wis.) and Stratagene (La Jolla, Calif.) and Ampli-Taq™ DNA polymerase, a recombinant Taq DNA polymerase available from Perkin-Elmer Cetus.

Generally, the synthesis will be initiated at the 3' end of each primer and proceed in the 5' direction along the template strand until the synthesis terminates, producing molecules of different lengths. There may be inducing agents, however, which initiate synthesis at the 5' end and proceed in the above direction using the same process.

The primer extension reaction product is subjected to a second primer extension reaction by treating it with a second polynucleotide synthesis primer having a preselected nucleotide sequence. The second primer is capable of initiating the second reaction by hybridizing to a nucleotide sequence, preferably at least about 20 nucleotides in length and more preferably a predetermined amount thereof with the first product preferably, a predetermined amount thereof to form a second primer extension reaction admixture. The admixture is maintained under polynucleotide synthesizing conditions for a time period, sufficient for the formation of a second primer extension reaction product.

PCR is carried out simultaneously by cycling, i.e., performing in one admixture, the above described first and second primer extension reactions, each cycle comprising polynucleotide synthesis followed by denaturation of the double stranded polynucleotides formed. Methods and systems for amplifying a specific nucleic acid sequence are described in U.S. Pat. Nos. 4,683,195, 4,683,202 and 4,800,159, to Mullis et al; and the teachings in *PCR Technology*, Ehrlich, ed. Stockton press (1989); Faloona et al., *Methods in Enzymol.* 155:335–50 (1987): *Polymerase Chain Reaction*, Ehrlich, eds. Cold Spring Harbor Laboratories Press (1989), the contents of which are hereby incorporated by reference.

For purposes of this invention, genetic diseases are diseases which include specific deletions and/or mutations in genomic DNA from any organism, such as, e.g., sickle cell anemia, cystic fibrosis, α-thalassemia, β-thalassemia, muscular dystrophy, Tay-Sachs disease, and the like. Cancer includes, for example, RAS oncogenes. Examples where reverse blot hybridization may be useful are provided by cystic fibrosis (CF) locus and RAS oncogenes. CF is one of the most common genetic diseases in Caucasian populations and more than 60 mutations have been found at this locus. Transforming mutations of RAS oncogenes are found quite frequently in cancers and more than 60 probes are needed to detect the majority of mutated variants. Analysis of CF and RAS mutants by conventional means is a difficult, complex and formidable task.

All of these genetic diseases may be detected by amplifying the appropriate sequence, digesting with UDG and analysis by reverse blot hybridization. In such a process, for example, a sample of DNA from, e.g., amniotic fluid containing a low level of the desired sequence is amplified, cut with UDG, and analyzed via a reverse blotting technique. Biotin-containing DNA probes are detected by chromogenic enzymes linked to avidin or biotin-specific antibodies.

Alternative methods suitable to analyze the unique UDG digested PCR product include gel electrophoresis on the basis of size or by sequencing methods. Furthermore, the UDG digest can render a dUTP-amplicon into a unique fragmentation pattern which can be analyzed on the basis of size (for example, electrophoresis) or by sequencing methods.

Hydrolysis of PCR amplicons with UDG is typically conducted at a temperature of at least 25° C., preferably at least about 37° C. for about 60 minutes; preferably at least about 10 minutes. The amount of UDG added is at least about 0.1 unit, preferably at least about 1 unit.

Typically, the PCR products are first heat denatured and next, quenched on ice prior to adding UDG. After UDG is added, the enzyme can be heated to about 95° C. for at least about 10 minutes. According to a preferred embodiment of this invention, hydrolysis of PCR amplicons with about 1 unit of UDG for about 10 minutes at temperature of about 37° C. can render DNA incapable of being copied by DNA polymerase. UDG can be 95% heat killed at 95° C. for about 10 minutes.

Typically, heat can be used to denature and cleave away unwanted uracil base, however, there are enzymes known to those skilled in the art that can also be use.

During the hydrolysis of the dUTP containing amplicon, an abundance of short oligonucleotide fragments are created. These oligonucleotides can be internally labeled (e.g., biotin-dCTP) during the course of the PCR reaction. The hybridization rate and signal intensity are enhanced using labeled oligo targets which are shorter than the full length PCR targets. The fragmentation pattern can also be predicted such that probes are designed for improved probe-target interaction.

The hybridization reaction mixture is formed by dilution of the UDG pcr hydrolyzate into SSC buffer at a final concentration of about 6×SSC containing 0.01% SDS.

The hybridization reaction mixture is maintained in the contemplated method under hybridizing conditions for a time period sufficient for the polynucleotide probe to hybridize to complementary nucleic acid sequences present in the sample to form a hybridization product, i.e., a complex containing probe and target nucleic acid.

Typical hybridizing conditions include the use of solutions buffered to pH values between 4 and 9, and are carried out at temperatures from 18° C. to 75° C., preferably at least about 22° C. to at least about 37° C., more preferably at least about 25° C. and for time periods from at least 0.5 seconds to at least 24 hours, preferably 10 min, although specific hybridization conditions will be dependent on the particular probe used.

Probe immobilization may be accomplished in different ways. In general, the attachment of standard oligonucleotides to unmodified glass or plastic surfaces is inefficient. The oligonucleotides are modified with molecules that promote adsorption or enable covalent attachment to the support. Oligonucleotides which are modified with bovine serum albumin adsorb passively to microtiter plates designed to bind protein molecules. (Cross et al., *Lancet*, 340:870–873 (1992)); Biotinylated oligonucleotides bind tightly to plates or beads that are coated with avidin or streptavidin. Oligonucleotides with polythymidylate tails have been photochemically crosslinked to nylon (Saiki et al., *PNAS*, 86:6230–6234 (1989)). More recently, oligonucleotides with terminal amino (Rasmussen et al., *Anal. Biochem.*, 198:138–142 (1991); Lund et al., *Nuc. Acid Res.*, 22:10861–10880 (1988)); or methyluridine groups have been covalently crosslinked to compatible reactive groups on multiwell plate surfaces (Khrapko, *J.DNA Sequencing Mapping*, 1:375–378 (1991). Polypropylene is preferred for construction of reverse hybridization arrays because it exhibits rather low adsorption of biopolymers such as proteins and nucleic acids. (Matson et al., *Anal. Biochem.*, 217:306–310 (1994)). The contents of the foregoing documents are hereby incorporated by reference.

Typical heterogeneous hybridization reactions include glass slides, nitrocellulose sheets and the like as the solid matrix to which the target containing nucleic acid fragments are affixed.

The invention is further demonstrated by the following illustrative examples, which should not be construed as a limitation on the scope of the present invention.

EXAMPLES

Example 1

FIGS. 1, 2 and Table 1 illustrate that both the sense and antisense strands of the 109 bp H-ras amplicon can be cut by UDG into a set of unique oligonucleotides. Certain of these fragments contain region where point mutations have occurred (bold text indicates base pairing region associated with mutation). Specific probes can be designed which will capture these fragments that identify the mutation. In Table I, for example, the sense strand oligonucleotide fragment 1A can be easily distinguished from fragment 1B by hybridization & washing stringency conditions, i.e., the mutation hybrid can be dissociated form the bound probe at least above 37° C. while the wild type dissociation requires a more elevated temperature, at least near 65° C. For the antisense pair, more stringent hybridization and wash conditions would be employed. However, a careful probe design would differentiate the 1-base mismatch (Td~25° C.) from the wild type (Td~37° C.).

Preparation of Biotinylated Amplicon

Plasmid DNA (0.1–0.2 ng) was amplified for H-RAS exon region in a 100 μl reaction volume containing 50 mM KCl, 10 mM Tris HCl, 1.5 mM MgCl$_2$, 0. 2 mM dATP, dGTP, dTTP (or 0.4 mM dUTP), and 0. 1 mM dCTP (Pharmacia) with 0.1 mM biotin-dCTP; 100 pmole amplification primer and 2 units of *Thermus aquaticus* (Taq) DNA polymerase (Perldn Elmer Cetus). The reaction was performed in a thermal cycler (Thermoline) using the cycle; denaturation at 91° C., 1 min., annealing at 56° C., 1 min. and extension at 72° C., 1 min. After 30 cycles, the samples were incubated for an additional 7 minutes at 72° C.

Agarose Gel Electrophoresis

PCR reactions (100 μL) were run according to the stated protocol for H-ras amplification with biotin-dCTP incorporation. Then, a 10 μL aliquot of the PCR was used for the UDG hydrolysis reaction (final volume, 25 μL). A 5 μL aliquot of the resulting UDG/PCR product was placed in wells along with 15 μL of running buffer (1×TBE): Wt=normal amplicon with dTTP; Δ=mutant amplicon with dTTP; Wt-U=normal amplicon with dUTP; Δ-U=mutant amplicon with dUTP. A 50 bp ladder was placed on each side of the samples and the gel run at 110 v for about 30 minutes.

As shown, Wt and Δ failed to digest, while Wt-U and Δ-U underwent complete digestion into short fragments which were visible as marked and estimated to be less than 50 bp. Primer-dimer at 50 bp was observed in normal amplicons but very little in the dUTP-amplicons.

Hybridization

10 μL of the UDG/PCR was mixed with 30 μL of deionized water and heated in a boiling water bath for about 10 minutes. After cooling on ice for 10 minutes, 1 μL of 1% SDS and 59 μL of 10×SSC was added and the entire sample puddled onto a glass microscope slide. The reverse hybridization strips (H-ras 17 E) contain at the top 2 lanes (bands) of 14 mer H-ras wild type (WT) probes followed by 2 lanes of 10 mer WT probes. The next 2 lanes contain 10 mer mutant (Δ) probes, followed by 2 lanes of 14 mer Δ probes. Hybridization was allowed to proceed for 1 hour at 25° C. After rinsing in 2×SSC, the hybridization strip was incubated in 100 μL of a streptavidin alkaline phosphatase solution (2.5 μg/mL in 2×SSC) for I hour. Following an extensive rinse in 2×SSC the signal was developed using the ELF reagent (Enzyme Labeled Fluorescence Phosphatase Detection Kit (Molecular Probes, Inc.). The signal was viewed on a UV-lightbox at 254 nm and the image captured using a CCD camera filtered at 530 nm. Signal were obtained for all samples. The hybridization signal intensity of Wt-U and Δ-U was significantly greater than that for the Wt and Δ amplicon controls. The signal intensity for the Wt-U, and more the Δ-U, were comparable to that of the wild type oligonucleotide control (A906) whose input concentration was set at 20 nM.

Figure 4:
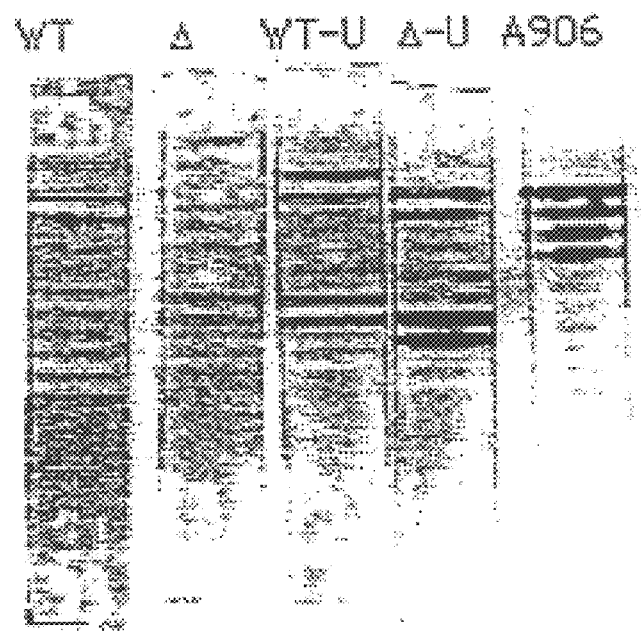
FIG. 4 illustrates a photograph after gel electrophoresis showing UDG fragment hybridization to H-ras reverse hybridization strip (H-ras 17E): Wt (strip 1), Δ (strip 2), Wt-U (strip 3) and Δ-U (strip 4). Strip 5 is the wild type oligonucleotide control (A906).

UDG digestion of the 109 bp H-ras amplicon which contained dUTP in place of dTTP generated fragments of less than 50 bp. FIG. 3 demonstrates that amplicons which did not contain dUTP could not be digested. Hybridization of normal amplicon and dUTP -amplicon internally labeled (with biotin-dCTP during the PCR reaction) has been conducted. FIG. 4 illustrates that the resulting signal intensity of the fragmented amplicon was significantly higher than that obtainable for the full length PCR product.

TABLE I

Predicted UDG Digest Fragmentation Pattern for 109bp H-ras dUTP-Amplicon

| Wild Type | Mutant |
|---|---|
| SENSE | |
| GACGGAA | |
| GGGCGCCGGCG (1A) | GGGCGCCG (1B) |
| 11mer | 8mer |
| GGGCAAGAG | |
| CCAGAACCA | |
| GGACGAA | |
| ACGACCCCAC | |
| antiSENSE | |
| CCACAAAA | |
| CAGCGCAC | |
| GCCCACACCGCCGGCGCCCACCACCACCAGC | |
| GCCCACAACGCCGGCGCCCACCACCACCAGC (1C) | (1D) |
| 31mer | 31mer |

Sequence: 1A (11mer, Td ~ 62.5° C.); 1B (8mer, Td ~ 37.7° C.)
1C (10mer, Td ~ 36.6° C.); 1D (10mer, Td ~ 32.3° C.)
(as mismatch to 1C, Td ~ 24.6° C.)

TABLE II

Predicted UDG Digest Fragmentation Pattern for 157 bp K-ras dUTP-Amplicon

| sense strand Wt-U/+ or Δ-U/+ |
|---|
| AGGCAAGAG |
| GGACGAA |
| CCAACAA |
| GCAGGACCA |

| antisense strand wt-U/- | Δ-U/- (same as wt, except where noted) |
|---|---|
| CAAAGAA | |

TABLE II-continued

Predicted UDG Digest Fragmentation Pattern
for 157 bp K-ras dUTP-Amplicon

AAAACAAG

GCACCAG

AAAACAAGA

CCACAAAA

CAAGGCAC

ACCACAAG

ACGCCACCAGC          ACGCCAaCAGC

11mer, Td ~ 41.2° C.   11mer, Td ~ 37.3° C.

mismatch ~ 30.3° C.    mismatch ~ 26.4° C.

(to mutation)          (to wild type)

TABLE III

Predicted UDG Digest Fragmentation Pattern
for 98/95mer ΔF508 dUTP-Amplicon sense strand
wt-U/+ or Δ-U/+

GGCACCA

AAAGAAAA

ACAGAAGCG

CAAAGCA

GCCAAC antisense strand
wt-U/-          Δ-U/- (same as wt, except where noted)

GCCAGGCA

CCAGGAAAAC aggaaacaccaAGA          aggaaacaccaa 15-mer, Td ~ 44.4° C.   12-mer, Td ~ 32° C.

12-mer, Td ~ 28° C.     9-mer, Td ~ 7.4° C.

Example 2 dUTP-amplicons were prepared for specific oligonucleotides, e.g. the K-ras SW480 mutation vs. wild type in which there is a C→A substitution at codon 12. In this case, 11 mers (Table II) are produced such that the mutation oligonucleotide is a 1-base mismatch that is substantially less stable (Td mismatch~30° C.) relative to the corresponding wild type hybrid (Td~40° C.). This trend further applies to the remaining additional mutations for the K-ras oncogene at codons 12/13.

Example 3

In another case such as exhibited by the Cystic Fibrosis ΔF508 mutation (Table III), unique oligomer fragments are produced for the wild type (15 mer, Td~44° C.) and mutant (12 mer, Td~32° C.). Probes can be designed to capture a specific sequence that can easily differentiate wild type for the mutation. For example, the probe complementary to a 12mer region of the wild type fragment (Td~28° C.) will only bind the corresponding 9 mer mutation fragment (Td~7° C. at a reduced temperature. In 51 of the most common CF mutations, 82% involved A and T substitutions or deletions: 18 (35%)T; 23(45%) A and 1(2%) an AT deletion. Thus, unique fragmentation patterns will be produced around the mutation site which can be identified via hybridization analysis.

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 11 base pairs
      (B) TYPE: nucleic acid
      (C) STRANDEDNESS: single
      (D) TOPOLOGY: linear (ii) MOLECULE TYPE: DNA (genomic)

(ix) SEQUENCE DESCRIPTION: SEQ ID NO: 1:

GGGCGCCGGC G                                                11

(2) INFORMATION FOR SEQ ID NO:2:

(i) SEQUENCE CHARACTERISTICS:
      (A) LENGTH: 8 base pairs
      (B) TYPE: nucleic acid
      (C) STRANDEDNESS: single
      (D) TOPOLOGY: linear (ii) MOLECULE TYPE: DNA (genomic)

(ix) SEQUENCE DESCRIPTION: SEQ ID NO: 2:

GGGCGCCG                                                    8

(2) INFORMATION FOR SEQ ID NO:3:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: DNA (genomic)

(ix) SEQUENCE DESCRIPTION: SEQ ID NO: 3:

GCCCACACCG CCGGCGCCCA CCACCACCAG C                        31

(2) INFORMATION FOR SEQ ID NO:4:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: DNA (genomic)

(ix) SEQUENCE DESCRIPTION: SEQ ID NO: 4:

GCCCACAACG CCGGCGCCCA CCACCACCAG C                        31

(2) INFORMATION FOR SEQ ID NO:5:

(i) SEQUENCE CHARACTERISTICS:
      (A) LENGTH: 11 base pairs
      (B) TYPE: nucleic acid
      (C) STRANDEDNESS: single
      (D) TOPOLOGY: linear (ii) MOLECULE TYPE: DNA (genomic)

(ix) SEQUENCE DESCRIPTION: SEQ ID NO: 5:

```
ACGCCACCAG C                                                                          11

(2) INFORMATION FOR SEQ ID NO:6:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(ix) SEQUENCE DESCRIPTION: SEQ ID NO: 6:

ACGCCAACAG C                                                                          11

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(ix) SEQUENCE DESCRIPTION: SEQ ID NO: 7:

AGGAAACACC AAAGA                                                                      15

(2) INFORMATION FOR SEQ ID NO:8:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(ix) SEQUENCE DESCRIPTION: SEQ ID NO: 8:

AGGAAACACC AA                                                                         12

(2) INFORMATION FOR SEQ ID NO:9:

(i) SEQUENCE CHARACTERISTICS:
        (A) LENGTH: 108 base pairs
        (B) TYPE: nucleic acid
        (C) STRANDEDNESS: single
        (D) TOPOLOGY: linear (ii) MOLECULE TYPE: DNA (genomic)

(ix) SEQUENCE DESCRIPTION: SEQ ID NO: 9:

GACGGAATAT AAGCTGGTGG TGGTGGGCGC CGGCGTGTGG GCAAGAGTGC                                 50

GCTGACCATC CAGCTGATCC AGAACCATTT TGTGGACGAA TACGACCCCA                                100

CTATAGAG                                                                             108

(2) INFORMATION FOR SEQ ID NO:10:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: DNA (genomic)

(ix) SEQUENCE DESCRIPTION: SEQ ID NO: 10:
```

```
CTCTATAGTG GGGTCGTATT CGTCCACAAA ATGGTTCTGG ATCAGCTGGA              50

TGGTCAGCGC ACTCTTGCCC ACACCGCCGG CGCCCACCA                          89
```

I claim:

1. A process for detecting the presence or absence of at least one specific nucleic acid sequence in a sample containing a nucleic acid or mixture of nucleic acids, or distinguishing between two different specific sequences in said sample, wherein the sample is suspected of containing said sequence or sequences, the process comprising the steps of:
   (a) treating the sample with one oligonucleotide primer for each strand of each different specific sequence under hybridizing and primer extension-labeling conditions whereby, for each strand of each at least one specific nucleic acid sequence or each specific sequence to which an oligonucleotide primer is hybridized, a labeled extension product of each primer is synthesized, which is complementary to each nucleic acid strand and is cleavable by a base excision repair enzyme,
   wherein said primer or primers are selected so as to be sufficiently complementary to each strand of each specific sequence to hybridize therewith;
   (b) treating the sample under denaturing conditions to separate the labeled primer extension products from their templates forming labeled single strands;
   (c) treating the sample with oligonucleotide primers whereby complementary labeled primer extension products are synthesized using each of the labeled single strands produced in step (b) as a template and using nucleoside triphosphates containing labeled members, resulting in amplification of the specific nucleic acid sequence or sequences if present;
   (d) digesting the product of step (c) with a base excision repair enzyme under conditions whereby labeled oligonucleotide fragments are produced;
   (e) in a reverse blot format adding the product of step (d) to at least one immobilized oligonucleotide probe which specifically hybridizes to each sequence being detected; and
   (f) determining whether hybridization of said product has occurred to thereby indicate the presence or absence of one or more specific nucleic acid sequences.

2. The process of claim 1, wherein the base excision repair enzyme is selected from the group consisting of DNA glycosylases, AP endonucleases and deoxyphosphodiesterases.

3. The process of claim 2, wherein the DNA glycosylase is selected from the group consisting of uracil-DNA glycosylase, 3-methyladenine DNA glycosylase, pyrimidine hydrate-DNA glycosylase, FaPy-DNA glycosylase and thymine mismatch-DNA glycosylase.

4. The process of claim 3, wherein the DNA glycosylase is uracil-DNA glycosylase.

5. The process of claim 1, wherein the labeled extension products of step (a) are synthesized using a synthesis mixture which comprises dUTP.

6. The process of claim 5, wherein the labeled extension products of step (a) are synthesized using a synthesis mixture which is free of dTTP.

7. The process of claim 1, wherein steps (b) and (c) are repeated at least once.

8. The process of claim 1, wherein steps (a) and (c) are accomplished by treatment with four different nucleoside triphosphates comprising dUTP and an agent for polymerization, which are added together with or separately from the primers.

9. The process of claim 1, wherein said nucleic acid is double stranded and its strand is separated by denaturing before or during step (a).

10. The process of claim 1, wherein the nucleic acid is a single stranded DNA.

11. The process of claim 9, wherein said nucleic acid is DNA and said primers are oligodeoxyribonucleotides.

12. The process of claim 10, wherein said nucleic acid is DNA and said primers are oligodeoxyribonucleotides.

13. The process of claim 1, wherein the specific nucleic acid sequence contains at least one deletion or mutation that causes a genetic disease.

14. The process of claim 13, wherein the genetic disease is cystic fibrosis.

15. The process of claim 1, wherein the specific nucleic acid sequence is contained in a pathogenic organism or is contained in an oncogene.

16. The method of claim 1, wherein the labeled product of step (d) is a biotinylated amplicon.

17. The method of claim 1, wherein probes are in an array.

18. A process for detecting the presence or absence of at least one specific nucleic acid sequence in a sample containing a nucleic acid or mixture of nucleic acids, or distinguishing between two different specific sequences in said sample, wherein the sample is suspected of containing said sequence or sequences, the process comprising the steps of:
   (a) treating the sample with one oligonucleotide primer for each strand of each different specific sequence under hybridizing and primer extension-labeling conditions whereby, for each strand of each at least one specific nucleic acid sequence or different specific sequence to which an oligonucleotide primer is hybridized, a labeled extension product of each primer is synthesized, which is complementary to each nucleic acid strand and is cleavable by uracil-DNA glycosylase,
   wherein said primer or primers are selected so as to be sufficiently complementary to each strand of each specific sequence to hybridize therewith;
   (b) treating the sample under denaturing conditions to separate the labeled primer extension products from their templates forming labeled single strands;
   (c) treating the sample with oligonucleotide primers whereby complementary labeled primer extension products are synthesized using each of the labeled single strands produced in step (b) as a template and using nucleoside triphosphates containing labeled members, resulting in amplification of the specific nucleic acid sequence or sequences if present;
   (d) digesting the product of step (c) with uracil-DNA glycosylase under conditions whereby labeled oligonucleotide fragments are produced;
   (e) in a reverse blot format adding the product of step (d) to at least one immobilized oligonucleotide probe which specifically hybridizes to each sequence being detected; and (f) determining whether hybridization of said product has occurred to thereby indicate the presence or absence of one or more specific nucleic acid sequences.

19. The process of claim 18, wherein the labeled extension products of step (a) are synthesized using a synthesis mixture which comprises dUTP.

20. The process of claim 18, wherein the labeled extension products of step (a) are synthesized using a synthesis mixture which is free of dTTP.

21. The process of claim 18, wherein steps (b) and (c) are repeated at least once.

22. The process of claim 18, wherein the specific nucleic acid sequence contains at least one deletion or mutation that causes a genetic disease.

23. The process of claim 18, wherein the genetic disease is cystic fibrosis.

24. The method of claim 18, wherein the labeled product of step (c) is a biotinylated amplicon.

25. A process for detection of a desired target nucleic acid sequence comprising the steps of:
   a) providing a sample containing the desired target nucleic acid sequence;
   b) incubating the sample with a base excision repair enzyme under conditions sufficient to permit the cleavage of the target nucleic acid sequence in the sample thereby forming base excision repair enzyme fragments;
   c) detecting the base excision repair enzyme fragments containing at least a portion of the target nucleic acid sequence by reverse blot hybridization.

26. A process for detection of a desired target nucleic acid sequence comprising the steps of:
   a) providing a sample containing the desired target nucleic acid sequence; said target nucleic acid sequence containing at least one dUTP residue;
   b) incubating the sample with uracil-DNA glycosylase under conditions sufficient to permit the cleavage of the target nucleic acid sequence in the sample thereby forming uracil-DNA glycosylate fragments;
   c) detecting the uracil-DNA glycosylase fragments containing at least a portion of the target nucleic acid sequence by reverse blot hybridization.

27. A process for detecting the presence or absence of a nucleic acid sequence containing a polymorphic restriction site associated with cystic fibrosis disease which sequence is suspected of being contained in a sample, the process comprising the steps of:
   (a) treating the samples at the same time or sequentially, with an oligodeoxyribonucleotide primer for each strand of said nucleic acid sequence, four different nucleoside triphosphates comprising dUTP, and an agent for polymerization under hybridizing and primer extension-labeling conditions, whereby for each strand of the nucleic acid sequence a labeled extension product of each primer is synthesized which is sufficiently complementary to each strand of the nucleic acid sequence being detected and which contains a region of the cystic fibrosis gene known to contain the polymorphic restriction site associated with cystic fibrosis, wherein said primers are selected whereby the labeled extension product synthesized from one primer, when it is separated from its complement, can serve as a template for synthesis of the labeled extension product of the other primer;
   (b) treating the sample under denaturing conditions to separate the labeled primer extension products formed if the sequence to be detected is present;
   (c) treating the product of step (b) as in step (a) with oligodeoxyribonucleotide primers, four different nucleoside triphosphates comprising dUTP, and an agent for polymerization whereby a labeled primer extension product is synthesized using each of the single strands produced in step (b) as a template, resulting in amplification of the sequence to be detected if present;
   (d) digesting the product of step (c) with uracil DNA glycosylase under conditions whereby the labeled oligonucleotide fragments are produced;
   (e) in a reverse blot format hybridizing the labeled oligonucleotide fragments of step (d) with an immobilized oligodeoxyribonucleotide probe complementary to a normal cystic fibrosis gene or a cystic fibrosis gene containing a polymorphic restriction site; and
   (f) determining by the presence or absence of hybridization whether the digest contains an oligonucleotide correlated with the presence of cystic fibrosis disease.

* * * * *